(12) United States Patent
Cerutti et al.

(10) Patent No.: US 6,337,182 B1
(45) Date of Patent: Jan. 8, 2002

(54) METHOD FOR THE QUANTITATIVE DETERMINATION OF DNA SEQUENCES

(75) Inventors: Peter A. Cerutti, Pully (CH); Emanuela Felley-Bosco, Bethesda, MD (US); Martha Sandy, Palo Alto, CA (US); Paul Amstad, Epalinges (CH); Jacob Zijlstra, Coppet (CH); Charareh Pourzand, Lausanne (CH)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 07/711,303

(22) Filed: Jun. 6, 1991

(30) Foreign Application Priority Data

Jun. 8, 1990  (EP) .............................................. 90110907

(51) Int. Cl.⁷ .......................... C12Q 1/68; C12P 19/34; C12N 15/12
(52) U.S. Cl. .......................... 435/6; 435/91.2; 435/455
(58) Field of Search ............................. 435/91, 6, 91.1, 435/91.2, 172.3, 455; 536/27, 23.5

(56) References Cited

FOREIGN PATENT DOCUMENTS

| EP | 0200362 A3 | 12/1986 | ............ C12Q/1/68 |
| EP | 0300796 A2 | 1/1989 | ............ C12Q/1/68 |

OTHER PUBLICATIONS

Maniatis et al., *Molecular Cloning: A Laboratory Manual*, Cold Spring Harbor Laboratory, 1982, p. 225.*
Scharf et al., *Science*, vol. 233, 1986, pp. 1076–1078.*
Gilliland et al., in *PCR Protocols: A Guide to Methods and Applications*, Innis et al. eds., Academic Press, 1990, pp. 60–69.*
Lyons, in *PCR Protocols: A Guide to Methods and Applications*, Innis et al., eds., Academic Press, 1990 pp. 386–391.*
Singer, *Cell.*, vol. 28, 1982, pp. 433–434.*
G. Deng, Nucl Acids Res. 16:6231 (1988).
J.M. Parry et al., Mutagenesis 5(3):209–212 (1990).
G. Gilliland et al., Proc. Natl. Acad. Sci. USA 87:2725–2729 (1990).
C.J. Farr et al., Proc. Natl. Acad. Sci. USA 85:1629–1633 (1988).
J. Zijlstra et al., A Mammalian Mutation System Avoiding Phenotypic Selection: The RFLP/PCR Approach, in Mutagens and Carcinogens in the Diet, pp. 187–200, M.W. Pariza et al. eds. Wiley–Liss, Inc. 1990.
E. Felley–Bosco et al., Nucl. Acids Res. 19:2913–2919 (1991).

* cited by examiner

Primary Examiner—James Ketter
(74) *Attorney, Agent, or Firm*—Finnegan, Henderson, Farabow, Garrett and Dunner, L.L.P.

(57) ABSTRACT

Method for the Quantitative Determination of DNA Sequences A method for the quantitative determination of DNA sequences containing at least one mutationally eliminated restriction site is disclosed in which the DNA sequences to be quantitatively determined are selectively amplified continuously eliminating any residual wild-type DNA sequences.

22 Claims, 2 Drawing Sheets

Fig. 1

HUMAN C-HA-RAS EXON 1

```
1646   5'GCAGGCCCCTGAGGAGCGATGACGGAATATAAGCTG 3'
         CGTCCGGGGACTCCTCGCTACTGCCTTATATTCGAC
                              └──── PRIMER 3
```

5' GCAGAATTCTGC / EcoRI

```
                              ├───┤ MspI
                                ├───┤ Codon 12
1682   GTGGTGGTGGGCGCCGGCGGTGTGGGCAAGAGTGC
       CACCACCACCCGCGGCCGCCACACCCGTTCTCACG 1717   GCTGACCATCCAGCTGATCCAGAACCATTTTGTG
       CGACTGGTAGGTCGACTAGGTCTTGGTAAAACAC
```

PRIMER 4 / GGTCTTAAGACG EcoRI

```
1751   GACGAATACGACCCCACTATAGAGGTGAGCCTGG
       CTGCTTATGGTGGGGTGATATCTCCACTCGGACC
```

| | | |
|---|---|---|
| MspI site | CCGG | (1695-1698) |
| CODON 12 | GGC | (1697-1699) |
| PRIMER 1 | | (1646-1665) |
| PRIMER 2 | | (1765-1784) |
| PRIMER 3 | | (1646-1665) EcoRI-tail |
| PRIMER 4 | | (1765-1784) EcoRI-tail |

Fig. 2

Taq I Site

```
        2499      2508 2511    2518
...TCC CCT ACA|TCG AGA CCT CG...
...AGG GGA TGT|AGC TCT GGA GC...
```

```
outer left primer 1
              2392
2373
GGG AGC AGA TCA AAC GGG TG...
CCC TCG TCT AGT TTG CCC AC...
```

Taq I standard

```
        2499      2508 2511    2518
...TCC CGT ACA|ACG TGA CCT CG...
...AGG GCA TGT|TGC ACT GGA GC...
```

```
         ...AG GGA GCA CTC ACT GAC
         ...TC CCT CGT GAG TGA CTG
                                 2610
             2591
             outer right primer 2
```

```
                       inner left primer 3
EcoRI tail   2401                         2420
AGT GAA TTC TCC GGA TGA CGT GCC CAT GGT GC...
         CCT ACT GCA CGG CTA CCA CG...
```

```
... GC TCT CCA CCC CAC AGC TAG
... CG AGA GGT GGG GTG TCG ATC GAT CTT AAG TGA
    2542                       2561   EcoRI tail
         inner right primer 4
```

METHOD FOR THE QUANTITATIVE DETERMINATION OF DNA SEQUENCES

The invention relates to a method for the quantitative determination of DNA sequences containing at least one mutationally eliminated restriction site in which the PCR-technology is applied.

The study of the formation and processing of chromosomal damage is of fundamental importance to many aspects of the life sciences including evolution, hereditary disease, carcinogenesis and possibly aging. Mutations in the form of deletions, insertions, rearrangements and base pair substitutions are hereditary consequences of spontaneous processes and the exposure to DNA damaging agents. Since mutation rates at low or no toxicity are in the range of $10^{-5}$ to $10^{-8}$ (for an average size target gene) the isolation of a mutated cell requires the selection of an altered phenotype. In most cases cells are isolated which have acquired the ability to grow in the presence of a particular drug. In all systems using phenotypic selection only mutations are recovered which have resulted in a selectable change in the function of the target protein or in its elimination altogether. This represents a severe limitation since many mutations remain functionally silent. Furthermore, only a few genes are suitable targets for drug selection. Drug resistance can be the consequence of a missense mutation or small in-frame deletion/insertion which renders the target protein inert to drug toxicity (e.g. resistance to cuabain). More useful are non-essential target genes/proteins which upon inactivation allow cell growth in the presence of a particular selecting drug because a wider spectrum of mutations can be obtained under these conditions. Target genes in this second category are X-linked hypoxanthineguanine-phosphoribosyl transferase (hgprt), bacterial xanthine-guanine-phosphoribosyl transferase (gpt), chromosomally integrated into hgprt$^3$ mammalian cells and adenine-phosphoribosyl transferase (aprt): hgprt and gpt-mutants are selectable with 6-thioguanine (6-TG) and aprt-mutants with 8-azaadenine (8-aza-A). By simply measuring the frequency of the generation of drug-resistant phenotypes, preferably coupled with the demonstration of a loss in the activity of the target enzyme, overall mutation frequencies can be obtained albeit without any information regarding the molecular event by which they arose.

The sophisticated protocols using molecular cloning of target genes from drug-resistant cells furnished insights into mutagenic mechanisms first in bacteria and then in mammalian cells over the last decade. Considerable progress was made with the help of shuttle vectors which allow the rescue of an extrachromosomal plasmid from mammalian cells, its amplification in bacteria and finally its sequencing by standard methodology. While important information has been gathered with this approach it has several serious disadvantages (e.g. the presence of variable numbers of copies of the vector per cell and its extrachromosomal location do not allow conclusions about the role of local chromosome- and DNA-structure on lesion-processing in mutagenesis). Work with bona fide shuttle vectors has been reviewed (Banbury Report 28 "Mammalian Mutagenesis" (1987); see in Friedberg and Hanawalt, eds. "Mechanisms and Consequences of DNA Damage Processing" (1989)) and is not further discussed.

An advanced shuttle vector system has been developed by Davidson et al. (Ashman and Davidson, (1987); Davidson et al. (1988); Greenspan et al. (1988)) who constructed a hgprt⁻ L-cell line with a chromosomally integrated bacterial gpt-gene (as part of a vector containing an SV40 origin). Cells mutated in the gpt-gene are selectable with 6-TG, the plasmid can be rescued and amplified by fusion with COS cells and then sequenced. Limitations of this system are relatively high spontaneous mutation frequencies ($>10^{-5}$) and the formation of gross rearrangements during vector recovery which necessitates the isolation of a. "majority plasmid" (with a "normal" restriction pattern); advantageous is the good recovery of deletions. Of particular interest is the study of the reversion of specific gpt mutations induced by ethylmethanesulfonate (EMS). This ethylating agent which modifies preferentially guanine residues specifically reverts mutations which have resulted from A•T →→→>G•C transitions or G•C→→→>C•G transversions. Reversion frequencies with 3.3mM EMS of a specific bp were 1–4×10$^{-5}$ (Greenspan et al. (1986)).

An analogous approach has also been taken by Tindall & Stankowski (Stankowski and Tindall (1987); Tindall and Stankowski (1987)) who compared the mutability of a chromosomally integrated bacterial gpt-gene to that of the endogenous hgprt-gene in chinese hamster ovary (CHO) cells. Much higher mutability of gpt was noted for clastogens, possibly because the flanking sequences at the insertion site of the gpt-gene are non-essential for viability.

Meuth et al. selected spontaneous (Nalbantoglu et al. (1986); Nalbantoglu et al. (1987)) or radiation induced (Breimer et al. (1987)) aprt mutants (with 8-aza-A) from a CHO line which is hemizygous for this small gene (3.8 kb). Either large deletions (detectable on Southern blots) or mutants which had gained or lost a restriction site (Southern/RFLP) were cloned and sequenced. Only relatively few mutations induced by ionizing radiation contained large deletions (6 out of 25); several deletions were flanked by direct repeats or at least one terminus was associated with a region of dyad symmetry. Spontaneous point mutations in aprt were mostly simple transitions and transversions. In contrast, ionizing radiation induced preferentially massive deletions in the hgprt-gene documenting locus specificity for mutations which are caused by the same mutagen.

An ingenious protocol for the analysis of 8-aza-A selected aprt mutants in CHO cells has been devised by Glickman et al.: Size-fractionated DNA is cloned into lambda which is then grown in a host containing a plasmid with flanking sequences of the hamster aprt-gene. This results in efficient recombinational transfer of the aprt-gene from lambda to the plasmid. The plasmid is rescued and sequenced using the M13 vector system. Spontaneous mutations were mostly G•C→A•T transitions. This could be due to cytosine deamination or reflect the fidelity of mammalian polymerases; all (except one) base-pair (bp) substitutions resulted in an amino acid change suggesting that protein structure and function co-determine the spectrum of mutants which are selected by 8-aza-A (De Jong et al. (1988)). Point mutations (i.e. no detectable changes on Southern blots because no relevant restriction sites were affected) induced by ionizing radiation were mostly simple transversions and transitions and small deletions. The latter were in some cases flanked by direct repeats (Grosovsky et al. (1988)). Ultraviolet light induced mutations were mostly targeted to dipyrimidine sites and consisted of G•C→→A•T transitions (Drobetsky et al. (1987)). Important general insights derive from this work. The fact that mutations in aprt were characteristic for a particular mutagen and distributed non-randomly points to a role for a chromatin/DNA "context". "Micro-environment" determines damage distribution, relative efficiency of error-free and error-prone repair, region- and site-specific repair, site specificity of polymerase fidelity, transcriptional activity etc. (Bohr et al. (1987)).

However, mutation distribution in phenotypically selected systems is also affected by protein selectable sites and protein functional hot spots.

A breakthrough in mutagenesis research (and many other aspects of molecular biology) arrived with the introduction of the polymerase chain reaction (PCR) which allows the potent amplification of single copy genes (or their transcripts) in unfractionated cellular DNA or even in crude cell lysates (Saiki et al. (1988); Mullis and Fallona (1987) and EP-A1 201 184, EP-A2 200 362, and EP-A1 237 362). PCR was also used to amplify gpt sequences in 6-TG-resistant AS52 cells (i.e. hgprt⁻ CHO cells with one copy of chromosomally integrated bacterial gpt). The amplified material was analyzed by direct sequercing. 40–45% of the spontaneous mutations consisted of small deletions with a 3 bp deletion hot spot and point mutations (the remaining 55–60% were large deletions detectable on Southern blots). The proneness of the gpt-gene in AS52 for deletions may be a consequence of its insertion into repetitive sequences. (Note: Spontaneous gpt mutations in E. coli are mostly point mutations).

PCR has also been applied to the analysis of hgprt-mutations by Skopek et al. (Simpson et al. (1988)). Because of the large size of the hgprt-gene a cDNA copy was first produced from RNA with reverse transcriptase (RT). Regions of the hgprt-cDNA were amplified and cloned into M13 for sequencing by standard procedures. Three ethylnitrosourea (ENU) induced mutations consisted of an A•T→G•C transition, an A•T→T•A transversion and an abnormal splice site (Vrieling et al. (1988)). A combination of PCR with denaturing gradient gel electrophoresis (DGGE) was applied by Thilly et al. for the analysis of hgprt-mutations in 6-TG selected human leucocytes (Cariello et al. (1988)). Hgprt-exon 3 was amplified by PCR connected to a GC-clamp and cleaved. Mutated exon 3 sequences were then separated from wild-type by DGGE. Mutated fragments were directly sequenced. Methyl-N-nitro-N-nitrosoguanidine (MNNG) and ICR 191 mutations were analyzed by this approach (Thilly, W., personal communication).

The ultimate goal remains the characterization of mutants in the intact animal rather than in cultured cells. Different cell types in a particular organ may differ in the metabolism of promutagens and in the processing of DNA lesions. Cell-cell interactions may affect mutagenic mechanisms. Only from in vivo mutation spectra in the human, safe conclusions can be reached concerning the type and concentrations of mutagens/carcinogens in our environment (Lohman et al. (1987); Delehanty (1986)). Ex vivo experiments with human T-lymphocytes have so far come closest to this goal. In a particular study 6-TG resistant T-cell clones from 8 donors were expanded in vitro with T-cell growth factor and major changes in the hgprt-gene were analyzed by Southern blotting. Approximately 10% of the 6-TG resistant clones had gross changes (Nicklas et al. (1986)). In a different approach by Mendelsohn et al., mutations in a cell surface protein are isolated by cell sorting (Delehanty et al. (1986)). Recently a shuttle vector system in transgenic mice has yielded first promising results for bona fide in vivo mutagenesis (Lohman et al. (1987)).

The isolation of spontaneous or xenobiotic-induced mutations at low toxicity represents a formidable task—spontaneous mutation frequencies (per average size target gene) being in the range of $10^{-8}$ (see e.g. Stankowski and Tindall (1987); Nalbantoglu et al. (1987); Nicklas et al. (1987)).

As discussed above, all presently available mammalian mutation systems require the isolation of cells which have acquired resistance to a selecting drug. This "phenotypic" selection is based either on the inactivation or activation, (resulting in decreased or increased drug resistance) of a particular target protein. Only a few genes can be used for this purpose—usually hemizygous genes which are not directly relevant to human disease (hgprt represents an exception). Many DNA sequence changes remain silent since only mutations which impair protein function can be monitored (except mutations at splice sites). Because of the need for drug selection at best ex vivo experiments can be carried out, since drug selection in the animal/human is not feasible. Ideally then a human mutation system should be designed which allows the quantitative study of any target gene on the molecular level directly in tissue biopsies. This requires the replacement of biological by biochemical selection of mutated gene sequences or polypeptides.

Thus, the technical problem underlying the present invention is to provide a fast and reliable biochemical assay for the quantitative determination of mutated gene (DNA) sequences.

The solution of this technical problem is achieved by providing the embodiments characterized in the attached set of claims.

Accordingly, the present invention relates to a method for the quantitative determination of DNA sequences containing at least one mutationally eliminated restriction site, comprising the following steps:

(a) isolation of DNA from a sample;

(b) mixing a defined amount of DNA obtained in step (a) with a defined amount of a DNA sequence used as an internal standard (hereinafter referred to as "standard DNA sequence") which does not contain in a cleavable form the restriction site corresponding to said mutationally eliminated restriction site;

(c) complete cleavage of the mixture of DNA sequences obtained in step (a) with a least a restriction enzyme recognizing the restriction site corresponding to the wild-type DNA sequence but being mutationally eliminated in the DNA sequence to be quantitatively determined;

(d) size fractionation of the DNA fragments obtained in step (c) and isolation of a fraction of DNA fragments containing the DNA sequence to be quantitatively determined;

(e) amplification of said DNA sequence to be quantitatively determined and of the standard DNA sequence by a method comprising the steps of:

(ea) carrying out about 25–50 PCR cycles, preferably about 40 to 50 PCR cycles, most preferably 40 to 45 PCR cycles, wherein said DNA sequence to be quantitatively determined and said standard DNA sequence are selectively amplified during at least the initial 10 to 15 PCR cycles while continuously eliminating any residual wild-type DNA sequences, and (eb) carrying out at least the last 3 PCR cycles, preferably at least the last 5 PCR cycles, and preferably not more than 10 PCR cycles with nested primers; and (f) quantitative determination of the amount of said DNA sequence containing at least one mutationally eliminated restriction site by comparison with the amount of said standard DNA sequence in the DNA fragments obtained by the amplification in step (e).

The term "imutationally eliminated restriction site" refers to a restriction site which occurs in the non-mutated wild-type DNA sequence of a given gene to be investigated, but which is eliminated by e.g. a point mutation in the mutated DNA sequence to be quantitatively determined. The PCR techniques applied in the method of the present invention are explained in detail e.g. in EP-A2 201 184. The term "nested primer" refers to primers which are complementary to sequences located towards the inside of a previously amplified fragment and, therefore, give rise to a shortened amplified DNA fragment.

The above method of the present invention is fast and reliable. It is of particular value because it permits the direct quantitative analysis of mutations in non-dividing human tissue explants, e.g. in biopsy samples or blood cell samples such as leucocytes. The method of the present invention can be applied to determine mutations in any gene of known structure, e.g. a proto-oncogene or a target gene for genetic disease in any organism. It can also be used to determine the level of background mutations in the general population. Furthermore, the method of the present invention can be applied in serial tests of potentially mutagenic or carcinogenic drugs in tissue cultures. In contrast to the present invention current bacterial and mammalian mutagenesis tests use target genes which are irrelevant to the etiology of cancer and genetic diseases. So far, the generally applied test for the determination of mutagenic or carcinogenic activities of a given drug is the Ames-test. However, this test suffers from the decisive disadvantage that it only is an indirect bacterial test and that laboratory animals have to be killed in order to obtain the necessary liver microsome fractions. Additionally, it has to be understood that none of the PCR-techniques known so far permitted a reliable quantitative analysis and determination of a low frequency of a mutated DNA sequence in the presence of a large excess of unaltered wild-type DNA. In existing methods wild-type and mutated sequences are coamplified and their relative frequencies remain unchanged in the amplification product. In addition, the low fidelity of Taq polymerase which is commonly used in PCR results in the introduction of artefactual mutations into the amplified sequences.

In a preferred embodiment the present invention relates to the above methods in which the quantitative determination in step (f) is effected by a dot blot hybridization in which probes are hybridized to a dilution series of the DNA fragments obtained by the amplification in step (e), said probes being specific for said DNA sequence to be quantitatively determined and for said standard DNA sequence.

Since the number of standard DNA molecules which had been added to genomic DNA at the outset is known, the frequency of a particular mutation can be estimated by comparison of the intensity of its signal on the dot blot with that of the standard.

In a further preferred embodiment of the method of the present invention the nested primers used in step (eb) carry restriction enzyme recognition sequences at their 51'-terminus, and the quantitative determination in step (f) is effected by carrying out the following additional steps:

(fa) preparation of recombinant vectors by cloning the DNA fragments obtained by the amplification in step (e) via their terminal restriction sites into a suitable vector;

(fb) transformation of host cells with the recombinant vectors obtained in step (fa);

(fc) cultivation of the transformed host cells obtained in step (fb) under suitable conditions;

(fd) quantitative determination of host cells in the culture which contain said DNA sequence to be quantitatively determined and of host cells in the culture which contain said standard DNA sequence, said determination being effected by hybridization with probes which are specific for said DNA sequence to be quantitatively determined and for said standard DNA sequence.

When effecting the cloning in step (fa), it may be necessary to cleave the vector and the PCR products with an appropriate restriction enzyme.

In a particularly preferred embodiment of the present invention the vector is a virulent bacteriophage and the determination in step (fd) is effected by plaque hybridization. Each individual bacteriophage plaque corresponds to a single type of mutation, to the standard DNA sequence, or to residual wild-type sequences. The frequency of each set of identified mutant plaques normalized by the frequency of standard plaques is a measure of relative mutation frequencies. Absolute mutation frequencies are obtained when the data is related to the amount of genomic DNA used in the test.

In a further particularly preferred embodiment of the present invention bacteriophages carrying the standard DNA sequence and/or bacteriophages carrying said DNA sequence to be quantitatively determined are used as (a) separate control(s). DNA sequences containing authentic mutations in the restriction site of choice can be synthesized in vitro, incorporated into a virulent bacteriophage and serve as positive controls for the selectivity of the plaque hybridization assay.

In another preferred embodiment the completeness of the cleavage in step (c) of the method of the present invention is ascertained by preparing a Southern Blot.

In a particularly preferred embodiment of the method of the present invention all amplification cycles in step (ea) are selectively eliminating any residual wild-type DNA sequences. The amplification product after each PCR cycle is restricted with an enzyme recognizing wild-type DNA which may have been synthesized on residual wild-type sequences still contained in the original sample. Since the amplified DNA fragment is usually short, e.g. about 200–350 base pairs and unmethylated, its digestion is particularly efficient.

In another particularly preferred embodiment of the method of the present invention the selective amplification continuously eliminating any residual wild-type DNA sequences is effected by using during each of the first 10–15 selective amplification cycles a restriction enzyme recognizing the restriction site corresponding to the wild-type DNA sequence but being mutationally eliminated in the DNA sequence to be quantitatively determined. A preferred restriction enzyme is the heat stable enzyme TaqI because it remains active during the PCR-cycles. Thus, in a particularly preferred embodiment of the present invention a combination of the enzymes Taq polymerase and TaqI is used. The selective elimination of wild-type DNA sequences is effected in this method independent of the methylation status of the DNA, since the PCR amplified DNA is usually not methylated.

In another preferred embodiment of the present invention said standard DNA sequence (A) is identical to the DNA sequence to be quantitatively determined except for at least two alterations allowing the discrimination of the standard DNA sequence over said DNA sequence to be quantitatively determined;

(B) has the same amplification efficiency as said DNA sequences to be quantitatively determined.

The standard DNA sequence is in this embodiment in all aspects identical to wild type except for 2–3 base pair changes at the DNA sequence to be quantitated. Therefore, the efficiency of its amplification is equal to that of wild-type DNA or of a particular mutation. The fact that the standard DNA contains at least 2 base pair changes at the site allows its distinction from bona fide single base pair mutations in the final colony- or plaque hybridization assay.

In a particularly preferred embodiment of the present invention, said sequence alterations of said standard DNA sequence are located in said restriction site being mutationally eliminated.

In another particularly preferred embodiment of the present invention said nested primers used in step (eb) carry EcoRI recognition sequences at their 5'-terminus. Inclusion of EcoRI sequences at the 5'-ends of the nested primers allows the facile cloning of the amplification product into standard cloning vectors. Since EcoRI sites are only used on the nested primers during the last PCR cycles (step (eb)) only the final PCR products become clonable eliminating some undesirable amplification products which may have formed in earlier cycles.

In a further preferred embodiment of the present invention the data obtained in step (f) are confirmed by DNA sequence analysis. When virulent bacteriophages are used as cloning vectors, the individual resulting plaque only harbors a single specific cloned DNA sequence. The DNA content of individual plaques is recovered and the cloned DNA sequenced by standard procedures confirming the results of plaque hybridization.

In a particularly preferred embodiment of the method of the present invention the polymerase used for said about 10 to 15 initial PCR cycles is the T4- or T7-polymerase. It is advantageous to use the T4- or T7-polymerase instead of the Taq-polymerase because their inherent fidelity in the amplification reaction is superior to that of Taq-polymerase. This reduces the danger of producing artefactual changes in the sequence to be determined during PCR, especially if the original sample of restricted genomic DNA contained residual, undigested wild-type sequences.

After 10–15 initial PCR cycles of high fidelity the bona fide mutated sequences to be determined have been sufficiently enriched so that Taq-polymerase can be used in the subsequent PCR cycles.

In another preferred embodiment of the present invention, the DNA sequence containing at least one mutationally eliminated restriction site is at least a part of a cancer related gene, preferably an oncogene, or of a gene related to a hereditary disease.

There are several cases where a mutational event which is related to the etiology of a human disease is accompanied by the loss of a restriction enzyme recognition sequence. Important examples are the mutational activation of the protooncogene c-Ha-ras. Mutational alterations of the tumor suppressor gene p53, of a tumor gene involved in the origin of retinoblastoma, and of a gene located on chromosome 18 q responsible for certain forms of colorectal carcinoma are additional cases in point in carcinogenesis. The Hemophilia Factor VIII gene and the al-antitrypsin Z gene represent examples where a hereditary disease in man is caused by a single base pair mutation which results in the elimination of an enzyme recognition site.

In a particularly preferred embodiment of the present invention, the oncogene is the Ha-ras gene.

In a further particularly preferred embodiment of the present invention, the oncogene is the human c-Ha-ras gene.

In a further particularly preferred embodiment of the present invention the restriction site which is mutationally eliminated in the Ha-ras oncogene is the MspI site located at codon 12 of this gene. In this case the restriction enzyme used during the selective amplification cycles is MspI or any isoschizomer thereof.

In another particularly preferred embodiment of the present invention the restriction site which is mutationally eliminated in the Ha-ras oncogene is the TaqI site located at nucleotide positions 2508 to 2511 being part of codons for isoleucine and glutamine in exon 3 of this gene. In this case the restriction enzyme used during the selective amplification cycles is TaqI or any isoschizomer thereof. However, using the heat-stable enzyme TaqI is advantageous because it remains active throughout the PCR cycles.

It has to be understood that unless indicated otherwise any numbers referring to PCR cycles which have to be effected when applying the method of the present invention are approximate values only, which may not be interpreted as particularly limiting the scope of the present invention. The person skilled in the art will be able to also apply this method with similar values providing essentially the same results which are therefore also part of the present invention.

THE FIGURES SHOW:

FIG. 1: Codon 12 region of exon 1 of the human c-Ha-ras gene with position of MspI restriction site and amplification primers. (SEQ ID NOS: 15, 16 and 17).

FIG. 2: Position of TaqI-endonuclease recognition site 2508–2511 of exon 3 of the human c-Ha-ras gene and of amplification primers.

The Examples illustrate the invention. Further information on the applied molecular biology techniques can be found in "Molecular Cloning, A Laboratory Manual" (2nd edition, 1989) by J. Sambrook, E. Fritsch & T. Maniatis.

EXAMPLE I

Rescue of 100 Human c-Ha-ras DNA Molecules Mutated at Codon 12 of Exon 1 from $10^9$ Human Wild-type c-Ha-ras Exon 1 Molecules The sensitivity of the method of the present invention for the quantitation of DNA sequences containing a mutationally eliminated restriction site is demonstrated with mixtures of plasmids containing a large excess of wild-type (wt) exon 1 of human c-Ha-ras (gly 12, GGC) and a small number of codon 12 mutated EJ c-Ha-ras (val 12, GTC) sequences isolated from a human bladder carcinoma. The two 5' residues of wt codon 12 are part of an MspI restriction site CCGG (1695–1698) which is lost upon mutation in EJ c-Ha-ras (see FIG. 1). Restriction with MspI plus HinfI yields a 272 bp fragment only from mutated EJ c-Ha-ras but two smaller fragments from the wt c-Ha-ras. Following exhaustive restriction the 200 to 350 bp fragment population is purified by gel electrophoresis and from the purified DNA a specific 138 bp fragment which encompasses the codon 12 region is amplified with Taq-polymerase and the 2 pairs of primers shown in FIG. 1. (Note: MspI restricted wt sequences are not amplified with the chosen primer pair). During the first 15 amplification cycles the amplification products are redigested with MspI after every cycle in order to minimize the amplification of residual wt-sequences. Only in the last few cycles primers 3 and 4 are used which contain non-complementary EcoRI recognition sequences facilitating subsequent insertion into a lambda gt10 cloning vector. The amplification mixtures are analyzed by dot blot hybridization with oligonucleotides specific for wt-(GGC) or mutated (GTC) codon 12 sequences, respectively, and by plaque hybridization following cloning into lambda gt10 bacteriophage.

The following experimental steps are performed:
1. Preparation of plasmid mixtures containing $10^9$ copies of pSVneo wt c-Ha-ras and 100 or 1000 copies of SP64 EJ mutated c-Ha-ras, respectively.
2. The plasmid mixtures are digested with 3U/µg DNA of MspI plus 3U/µg DNA of HinfI according to conditions specified by the supplier of the enzymes (e.g. Boehringer Mannheim).
3. A 200–350 bp fragment population is isolated from the digestion mixture by electrophoresis on a 2% preparative agarose gel and eluted from the gel cut with a "Biotrap" apparatus (Schleicher and Schull). Completion of digestion and the yield of recovery of diagnositic c-Ha-ras gene fragments:s is monitored by Southern blotting using a short probe in the region which will be amplified.
4. Amplification for 15 cycles of a specific 138 bp fragment from the DNA preparation described in (3) encompassing (mutated) codon 12 of c-Ha-ras exon 1 with Taq-polymerase (1U) using the primers 1 and 2 shown in FIG. 1 which lack clonable EcoRI-tails. The cycles consist of consecutive incubations for 85 secs. at 92° C., 95 secs. at 60° C. and 30 min. at 37° C. During the incubation at 37° C. 0.7 U of fresh MspI-enzyme is added for every cycle. The total reaction mixture is 25 µl General amplification conditions are as outlined below in Example II (see also in "PCR Technology", H. A. Erlich, ed., Stockton Press, N. Y. 1989).
5. Continuation of the amplification after addition of 1U of fresh Taq polymerase for an additional 20 cycles with incubations only for 85 secs. at 92° C. and 95 secs. at 60° C.
6. Continuation of the amplification with 1U of fresh Taq polymerase of an aliquot of the amplification mixture with clonable primers 3 and 4 containing EcoRI-tails (see FIG. 1) for 5 to 10 cycles using the incubation conditions outlined in (5).
7. Purification and digestion of amplified DNA: Removal of primers by passage through QIAGEN tip 5 (DIAGEN; Inst. fur molekularbiologische Diagnostik GmbH, Dusseldorf; standard protocol for "Removal of linker DNA from DNA fragments", provided by the supplier). The QIAGEN purified DNA is then digested with a mixture of MspI plus EcoRI in order to further remove residual wt-sequences and to generate single-stranded, clonable EcoRI tails. The DNA is repurified on QIAGEN-tip 5 and precipitated with isopropanol in the presence of 2 µg t-RNA carrier.
8. Analysis of the amplified DNA by dot blot hybridization with $^{32}$P-labeled synthetic oligonucleotides (20-mers) encompassing c-Ha-ras codon 12, which are complementary to the wt-sequence (codon 12: G(;C) or EJ c-Ha-ras (codon 12:GTC), respectively, according to standard protocols (see "Current Protocols in Molecular Biology" Vol. 1 and 2, eds. F. Ausubel et al., Greene Publishing Assoc. and Wiley Interscience, 1986).
9. Alternatively, the amplified DNA is cloned into lambda gt10, the DNA packaged and *E. coli* C600 Hfl indicator bacteria are infected with the bacteriophage (acc. to PROMEGA BIOTEC; Madison, Wis., protocol 025). The infected bacteria are plated, the resulting plaques blotted to Colony/Plaque Screen filters (Dupont, NEN Research product no. NEF-978) and analyzed by probing with the specific, $^{32}$P-labeled oligonucleotides described under (6) according to standard procedures.

In a specific experiment the following representative results were obtained by plaque hybridization.
(a) Of approximately 100 plaques per replica Petri dish 35 to 45 contained the wt-tetranucleotide sequence CCGG (1695–1698) which is recognized by MspI. These plaques presumably originate from residual undigested wt-plasmid regardless of the composition of the original plasmid mixture.
(b) For an initial mixture of $10^3$ copies of mutated EJ c-Ha-ras plus $10^9$ copies of wt c-Ha-ras 57–65 of a total of 100 plaques contained the sequence of the EJ-mutation CCGT (1695–1698) which is resistant to MspI digestion.
(c) For an initial mixture of $10^2$ copies of mutated EJ c-Ha-ras plus $10^9$ copies of wt c-Ha-ras 35 to 40 of a total of 100 plaques contained the EJ-mutation.

It follows that the method of the present invention is capable of detecting better than one mutated copy of codon 12 c-Ha-ras in the presence of $10^7$ copies of wt c-Ha-ras.

EXAMPLE II

A. Detection of Ethylnitrosourea Induced Mutations in the TaqI-endonuclease Site TCGA (2508–2511) of Exon 3 of the c-Ha-ras Gene in Cultured Human Fibroblasts Monolayer cultures of human foreskin fibroblasts 3229 (other cell lines of the same origin work equally well) are treated with the carcinogen ethylnitrosourea (ENU, 2mM) in DMSO or sham-treated with DMSO only and harvested 3 days later. Total DNA is extracted and digested exhaustively with BamHI yielding a 6.6 Kb fragment containing the c-Ha-ras gene. The digestion mixture is separated on a 1% agarose gel and the DNA in the region from 6.0–7.0 Kb eluted in a "Biotrap" apparatus as described in Example I. The completeness of the BamHI digestion and the recovery of the c-Ha-ras sequences from the gel are monitored by Southern-blotting with a 6.6 Kb c-Ha-ras probe. "Biotrap" purified DNA (6.0–7.0 Kb, corresponding to 25 µg BamHI digested genomic DNA) is then exhaustively digested with TaqI endonuclease and a fragment containing the TaqI site 2508–2511 (TCGA) of the c-Ha-ras gene amplified as described below and illustrated in FIG. 2. At the outset of the amplification 10 copies of an authentic "standard" sequence are added which contain the sequence ACGT at residues 2508–2511 (and a G-instead of the C residue at position 2503), but are otherwise identical to wt c-Ha-ras.

B. Selective Amplification of Mutated TaaI-endonuclease Site TCGA (2508–2511) of Exon 3 of the Human c-Ha-ras Gene The digested DNA was amplified, utilizing a "nested primer approach" to selectively amplify only DNA containing a mutated TaqI restriction site.
1. Amplification Cycles 1–15. The cycles 1–15 were conducted with the outer primers (see FIG. 2) yielding a 237 bp fragment. Each cycle consists of a melting temperature of 81° C. (1.1 min), an annealing temperature of 55° C. (0.8 min), and an extension temperature of 65° C. (0.3 min). The initial contents of each amplification tube are as follows: 2.5 µl of "digested DNA" (i.e. TaqI digested 6.0–7.0 Kb BamHI fragment population described above); 0.75 µg of each outer primer (primers 1 and 2, see FIG. 2); 25 mM each of dATP, dCTP, dGTP and dTTP; 21% DMSO; 66.6 mM Tris-HCl, pH 8.8, 16.6 mM ammonium sulfate; 6.7 mM magnesium chloride; 10 mM 2-merc:aptoethanol, 6.7 µM EDTA, and 1.5 units Taq polymerase, in a total volume of 25 µl. To prevent evaporation during temperature cycling, an overlay of 3–4 drops of paraffin oil is added to each tube. (Note: Taq polymerase is added to the tubes after an initial melting period of 3 minutes at 92° C. Subsequently, one µl additions of a TaqI endonuclease-containing TaqI Mix are made to the appropriate amplification tubes during the annealing periods of cycles 1, 3, 5, 7, 9, 11, 13 and 15). The TaqI mix contains 25 mM each of DATP, dCTP, dGTP and dTTP; 21% DMSO; 66.6 mM Tris-HCl, pH 8.8; 16.6 mM ammonium sulfate; 6.7 mM magnesium chloride; 10 mM 2-mercaptoethanol; 6.7 µm EDTA; 0.12 units/µl Taq polymerase and 1.2 units/µl TaqI endonuclease.

2. Cycles 16–25

Amplification cycles 16–25 are conducted at a higher melting temprature (91° C.) and a lower DMSO concentration (12%) with the outer primers (primers 1 and 2, see FIG. 2). Each cycle consists of a melting temperature of 91° C. (0.8 min) and an annealing temperature of 57° C. (0.4 min). After the 15th cycle, the DMSO concentration is reduced to 12% by transferring 16 µl of each amplification solution to new tubes which contain 11 µl of a DMSO-free mixture consisting of 229 ng of each outer primer/11 µl; 25 mM each of dATP, dCTP, dGTP and dTTP; 66.6 mM Tris-HCl, pH 8.8; 16.6 mM ammonium sulfate; 6.7 mM magnesium chloride, 10 mM 2.-mercaptoethanol and 6.7 µM EDTA. Paraffin oil (3 drops) is added to each tube and the 16th cycle begun with an initial melting period of 3 min at 92° C., after which 1.5 units of Taq polymerase is added to each tube.

3. Cycles 26–41

Amplification cycles 26–41 are conducted with the inner primers (primers 3 and 4, see FIG. 2), which contain "EcoRI tails" to facilitate later ligation into phage arms. With the chosen inner primers a 184 bp fragment is synthesized. In order to reduce competition between outer and inner primers, the outer primer concentration is reduced by a factor of 121 relative to the inner primer concentration.

After the 25th cycle, 3 µl of each amplified solution are diluted with 45 µl TE. 10 µl of each TE-diluted amplification mixture are then transferred to new tubes and amplified in the presence of inner primers in a total volume of 40 µl. In addition to the TE-diluted amplified material, each amplification tube contains 1.6 µg of each inner primer, 25 mM each dATP, dCTP, dGTP and dTTP; 12% DMSO: 66.6 mM Tris-HCl, pH 8.8, 16.6 mM ammonium sulfate: 6.7 mM magnesium chloride; 10 mM 2-mercaptoethanol, 6.7 µM EDTA. Paraffin oil (3 drops) is added to each tube. Subsequent cycles consist of a melting temperature of 91° C. (0.8 min) and an annealing temperature of 57° C. (0.4 min).

C Purification of Amplified DNA and Determination of Mutations in the TaqI-endonuclease Site TCGA (2508–2511) of Exon 3 of the Human c-Ha-ras Gene The procedures are analogous to steps (7) to (9) described above in Example I, but adapted to the analysis of the particular TaqI endonuclease site. Important specific experimental conditions are listed below.

1. Purification of amplified DNA (compare step (7) of Example I): The QIAGEN-purified DNA is digested with a mixture of TaqI plus EcoRI-enclonuclease and then repurified on QIAGEN tip 5 and precipitated with isopropanol in the presence of 24 µg t-RNA carrier.

2. Dot-blot hybridization with synthetic oligonucleotides encompassing the TaqI endonuclease site (2508–2511): A set of 12 different $^{32}$P-labeled oligonucleotide probes (20-mers) are used which differ only in the sequence at the TaqI-site (but contain identical flanking sequences) in order to detect the 12 possible base-pair mutations; in addition a wt-oligonucleotide and a TaqI "standard" oligonucleotide are used for the detection of wt-sequences and rescued TaqI "standard" molecules. Dot-blot procedures are as reported in the literature.

3. Plaque hybridization with synthetic oligonucleotides encompassing the TaqI endonuclease site (2508–2511): The amplified DNA is cloned into lambda gt10 and plaques formed on the indicator strain *E. coli* C600 Hfl are analyzed with the set of specific $^{32}$P-labeled oligonucleotide probes described in (2). Individual washing temperatures following hybridization are determined for each oligonucleotide probe in order to establish specificity of interaction with the predicted mutated, wt- or "standard" TaqI recognition sequence. For this purpose fragments of the c-Ha-ras gene were constructed in vitro which contain only a single, authentic sequence change at the TaqI-endonuclease site (2508–2511) and cloned into lambda gt10. Lambda plaques containing exclusively a known DNA sequence are blotted to colony plaque screen filters. These filters are then used to establish the stringency of the washing conditions.

TABLE 1

Selective washing temperatures for the wt-, "standard" and 12 mutant probes:

| | OLIGONUCLEOTIDE SEQUENCE 2508-2511 | WASHING TEMPERATURE ° C. |
|---|---|---|
| Wild type | TCC CCT ACA TCGA GA CCT CG | 64 |
| Standard mutant construct | TCC CGT ACA ACGT GA CCT CG | 64 |
| Single base pair mutants | TCC CCT ACA TCGT GA CCT CG | 58 |
| | TCC CCT ACA TCGG GA CCT CG | 61 |
| | TCC CCT ACA TCGC GA CCT CG | 61 |
| | TCC CCT ACA ACGA GA CCT CG | 58 |
| | TCC CCT ACA CCGA GA CCT CG | 62 |
| | TCC CCT ACA GCGA GA CCT CG | 62 |
| | TCC CCT ACA TAGA GA CCT CG | 56 |
| | TCC CCT ACA TTGA GA CCT CG | 57 |
| | TCC CCT ACA TGGA GA CCT CG | 59 |
| | TCC CCT ACA TCAA GA CCT CG | 57 |
| | TCC CCT ACA TCTA GA CCT CG | 62 |
| | TCC CCT ACA TCCA GA CCT CG | 59 |

In a particular experiment using the described methodology the following results were obtained for base pair mutations in the TaqI-endonuclease site 2508–2511 of exon 3 of the c-Ha-ras gene:

| A. DNA from untreated 3 × 10[6] human fibroblasts (3229) | |
|---|---|
| Plaques per Petri dish | plaques containing standard-sequence ACGT |
| 202 | 24 (11.8%) |
| 166 | 33 (19.9%) |

No plaques were detected which contained wt-DNA or any of the 12 possible base pair mutations.

B. DNA from 3 × 10[6] human fibroblasts (3229) treated with 2 mM ethylnitrosourea

| Plaques per Petri dish | plaques containing standard-sequence ACGT | plaques containing mutated sequence TCTA |
|---|---|---|
| 200 | 25 (12.5%) | 16 (8%) |
| 200 | 29 (19.5%) | 13 (6.5%) |

-continued

| | | |
|---|---|---|
| 159 | 35 (22%) | 12 (7.5%) |
| 197 | 28 (14.2%) | 12 (6%) |
| $\overline{m}$ | 31.7 (17%) | 13.2 (7%) |

No plaques were detected which contained the wt sequence DNA or any of the remaining 11 possible base-pair mutations. From these data the frequency of the ethylinitrosourea induced base-pair mutation TCGA→TCTA at the sequence 2508–2511 of the human c-Ha-ras gene was estimated at 7.5 mutations in $10^7$ c-Ha-ras genes. (Note: 25 μg of DNA from diploid human fibroblasts correspond to approximately $4\times10^6$ copies of the c-Ha-ras gene; since 10 copies of standard sequence added at the outset gave rise to 17% standard containing plaques the observed 7% of the plaques containing the mutation TCTA corresponds to 6 copies of this mutated sequence in the original DNA sample. Therefore, the mutation frequency is estimated at $7.5\times10^{-7}$ per c-Ha-ras gene).

What is claimed is:

1. A method for the quantitative determination of a mutant DNA sequence containing at least one mutationally eliminated restriction site, comprising the following steps:
   (a) isolation of DNA from a sample;
   (b) mixing a defined amount of DNA obtained in step (a) with a defined amount of a standard DNA sequence which does not contain in a cleavable form the restriction site corresponding to said mutationally eliminated restriction site to obtain a mixture of DNA sequences;
   (c) complete cleavage of the mixture of DNA sequences obtained in step (b) with at least one restriction enzyme recognizing the restriction site corresponding to the wild-type DNA sequence but being mutationally eliminated in the DNA sequence to be quantitatively determined in order to obtain DNA fragments;
   (d) size fractionation of the DNA fragments obtained in step (c) and isolation of a fraction of DNA fragments containing the DNA sequence to be quantitatively determined;
   (e) amplification of said DNA sequence to be quantitatively determined and of said standard DNA sequence by a method comprising the steps of:
      (ea) carrying out about 25 to 50 PCR amplification cycles, wherein said DNA sequence to be quantitatively determined and said standard DNA sequence are selectively amplified during at least the initial 10 to 15 PCR amplification cycles while continuously eliminating any residual wild-type DNA sequences, and
      (eb) carrying out at least the last 3 PCR amplification cycles with nested primers; and
   (f) quantitative determination of the amount of said DNA sequence containing at least one mutationally eliminated restriction site by comparison with the amount of said standard DNA sequence in the DNA obtained by the amplification in step (e).

2. The method according to claim 1, wherein the quantitative determination in step (f) is effected by a dot blot hybridization in which probes are hybridized to a dilution series of the DNA obtained by the amplification in step (e), said probes being specific for said DNA sequence to be quantitatively determined and for said standard DNA sequence.

3. The method according to claim 1, wherein the nested primers carry restriction enzyme recognition sequences at their 5'-terminus and wherein the quantitative determination in step (f) is effected by carrying out the following additional steps:
   (fa) preparation of a recombinant vector by cloning the DNA fragments obtained by the amplification in step (e) via their terminal restriction sites into a suitable vector;
   (fb) transformation of host cells with the recombinant vectors obtained in step (fa);

(fc) cultivation of the transformed host cells obtained in step (fb) under suitable conditions;

(fd) quantitative determination of host cells in the culture which contain said DNA sequence to be quantitatively determined and of host cells in the culture which contain said standard DNA sequence, said determination being effected by hybridization with probes which are specific for said DNA sequence to be quantitatively determined and for said standard DNA sequence.

4. The method according to claim 1 wherein the PCR products are once more cleaved, before said quantitative determination of step (f), with said restriction enzyme recognizing the restriction site corresponding to the wild-type DNA sequence, but being mutationally eliminated in the DNA sequence to be quantitatively determined.

5. The method according to claim 3 wherein the vector is a virulent bacteriophage and the determination in step (fd) is effected by plaque hybridization.

6. The method according to claim 1 wherein bacteriophages carrying the standard DNA sequence and/or bacteriophages carrying said DNA sequence to be quantitatively determined are used as separate controls.

7. The method according to claim 1 wherein the completeness of the cleavage in step (c) is ascertained by control on a Southern Blot.

8. The method according to claim 1 wherein all amplification cycles in step (ea) setectively eliminate any residual wild-type DNA sequences.

9. The method according to claim 1 wherein the amplification continuously eliminating any residual wild-type DNA sequences is effected by using during each of said amplification cycles in step (ea) a restriction enzyme recognizing the restriction site corresponding to the wild-type DNA sequence but being mutationally eliminated in the DNA sequence to be quantitatively determined.

10. The method according to claim 9 wherein the restriction enzyme is TaqI.

11. The method according to claim 1 wherein said standard DNA sequence (a) is identical to the DNA sequence to be quantitatively determined except for a first and a second nucleotide alteration allowing the discrimination of the standard DNA sequence over said DNA sequence to be quantitatively determined;

(b) has the same amplification efficiency as said DNA sequence to be quantitatively determined; and (c) wherein said first nucleotide alteration in said restriction site is used to discriminate said mutant from said wild-type and said second nucleotide alteration eliminates a restriction site from said sequence to be quantitatively determined, which restriction site is different from that used to discriminate said wild-type from said mutant.

12. The method according to claim 1 wherein said standard DNA sequence (a) is identical to the DNA sequence to be quantitatively determined except for at least three alterations allowing the discrimination of the standard DNA sequence over said DNA sequence to be quantitatively determined;

(b) has the same amplification efficiency as said DNA sequence to be quantitatively determined; and (c) wherein one of said alterations is in said restriction site used to discriminate said mutant from said wild-type and another of said alterations eliminates a restriction site from said sequence to be quantitatively determined, which restriction site is different from that used to discriminate said wild-type from said mutant.

13. The method according to claim 3 wherein said nested primers used in step (eb) carry EcoRI recognition sequences at their 5'-terminus.

14. The method according to claim 1 wherein the said about 10 to 15 initial PCR amplification cycles use T4- or T7-DNA polymerase.

15. The method according to claim 1 wherein the DNA sequence containing at least one mutationally eliminated restriction site is at least a part of a cancer related gene, or a gene related to a hereditary disease.

16. The method according to claim 15, wherein the cancer related gene is an oncogene.

17. The method according to claim 16, wherein the oncogene is the Ha-ras gene.

18. The method according to claim 17, wherein the restriction site which is mutationally eliminated is the MspI site located at codon 12 of the Ha-ras gene.

19. The method according to claim 17, wherein the restriction site which is mutationally eliminated is the TaqI site located at nucleotide positions 2508 to 2511 in exon III of the Ha-ras gene.

20. The method according to claim 19 wherein the restriction enzyme recognizing the restriction site corresponding to the wild-type DNA sequence but being mutationally eliminated in the DNA sequence to be quantitatively determined is TaqI or any isoschizomer thereof.

21. The method according to claim 1, wherein the amplification in step (ea) comprises carrying out about 40 to 50 PCR amplification cycles.

22. The method according to claim 17, wherein the restriction enzyme recognizing the restriction site corresponding to the wild-type DNA sequence but being mutationally eliminated in the DNA sequence to be quantitatively determined is MspI or any isoschizomer thereof.

* * * * *

UNITED STATES PATENT AND TRADEMARK OFFICE
CERTIFICATE OF CORRECTION

PATENT NO. : 6,337,182 B1
DATED : January 8, 2002
INVENTOR(S) : Peter A. Cerutti et al.

It is certified that error appears in the above-identified patent and that said Letters Patent is hereby corrected as shown below:

Column 21,
Line 26, "setectively" should read -- selectively --.

Column 22,
Line 46, "claim 17" should read -- claim 18 --.

Signed and Sealed this

Third Day of September, 2002002

Attest:

JAMES E. ROGAN
Attesting Officer    Director of the United States Patent and Trademark Office

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

TCCCCTACAT CGAGACCTCG      20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TCCCGTACAA CGTGACCTCG      20

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

TCCCCTACAT CGTGACCTCG      20

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

TCCCCTACAT CGGGACCTCG                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TCCCCTACAT CGCGACCTCG                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCCCCTACAA CGAGACCTCG                    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCCCCTACAC CGAGACCTCG                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TCCCCTACAG CGAGACCTCG                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TCCCCTACAT AGAGACCTCG                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TCCCCTACAT TGAGACCTCG                                       20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TCCCCTACAT CAAGACCTCG                                       20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TCCCCTACAT CTAGACCTCG                                       20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TCCCCTACAT CCAGACCTCG                                       20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TCCCCTACAT GGAGACCTCG                                       20

(2) INFORMATION FOR SEQ ID NO:15:

(i) SEQUENCE CHARACTERISTICS:
        (A) LENGTH: 139 base pairs

```
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:15:

GCAGGCCCCT GAGGAGCGAT GACGGAATAT AAGCTGGTGG TGGTGGGCGC CGGCGGTGTG      60

GGCAAGAGTG CGCTGACCAT CCAGCTGATC CAGAACCATT TTGTGGACGA ATACGACCCC     120

ACTATAGAGG TGAGCCTGG                                                  139

(2) INFORMATION FOR SEQ ID NO:16:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:16:

GCAGAATTCT GC                                                          12

(2) INFORMATION FOR SEQ ID NO:17:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:17:

GGTCTTAAGA CG                                                          12
```